US011423678B2

(12) United States Patent
Soans et al.

(10) Patent No.: US 11,423,678 B2
(45) Date of Patent: Aug. 23, 2022

(54) AUTOMATED WHOLE-SLIDE IMAGE CLASSIFICATION USING DEEP LEARNING

(71) Applicant: PROSCIA INC., Philadelphia, PA (US)

(72) Inventors: Rajath Elias Soans, Philadelphia, PA (US); Julianna Ianni, Philadelphia, PA (US); Sivaramakrishnan Sankarapandian, Philadelphia, PA (US)

(73) Assignee: PROSCIA INC., Philadelphia, PA (US)

( * ) Notice: Subject to any disclaimer, the term of this patent is extended or adjusted under 35 U.S.C. 154(b) by 214 days.

(21) Appl. No.: 17/028,069

(22) Filed: Sep. 22, 2020

(65) Prior Publication Data

US 2021/0090250 A1    Mar. 25, 2021

Related U.S. Application Data

(60) Provisional application No. 62/904,146, filed on Sep. 23, 2019, provisional application No. 62/904,263, filed on Sep. 23, 2019.

(51) Int. Cl.
*G06V 20/69* (2022.01)
*G06N 3/04* (2006.01)
(Continued)

(52) U.S. Cl.
CPC ............ *G06V 20/695* (2022.01); *G06K 9/627* (2013.01); *G06K 9/628* (2013.01); *G06K 9/6256* (2013.01);
(Continued)

(58) Field of Classification Search
CPC ...... G06V 10/82; G06V 20/69; G06V 20/695; G06V 20/698; G06V 40/162;
(Continued)

(56) References Cited

U.S. PATENT DOCUMENTS 10,453,197 B1   10/2019   Cholakkal et al.
11,309,074 B2    4/2022   Ceballos Lentini et al.
(Continued)

FOREIGN PATENT DOCUMENTS

CN      110309832 A    10/2019
WO   2019/084697 A1     5/2019
(Continued)

OTHER PUBLICATIONS

Extended European Search Report issued in corresponding European Application No. 20197903.6, 9 pages.
(Continued)

*Primary Examiner* — Nay A Maung
*Assistant Examiner* — Jose M Torres
(74) *Attorney, Agent, or Firm* — MH2 Technology Law Group LLP

(57) ABSTRACT

Computer-implemented techniques for classifying a tissue specimen are presented. The techniques include obtaining an image of the tissue specimen; segmenting the image into a first plurality of segments; selecting a second plurality of segments that include at least one region of interest; applying an electronic convolutional neural network trained by a training corpus including a set of pluralities of tissue sample image segments, each of the pluralities of tissue sample image segments labeled according to one of a plurality of primary pathology classes, where the plurality of primary pathology classes consist of a plurality of majority primary pathology classes, where the plurality of majority primary pathology classes collectively include a majority of pathologies according to prevalence, and a class for tissue sample image segments not in the plurality of majority primary pathology classes, such that a primary pathology classification is output; and providing the primary pathology classification.

20 Claims, 10 Drawing Sheets

(51) Int. Cl.

| | |
|---|---|
| *G06N 3/08* | (2006.01) |
| *G06T 7/11* | (2017.01) |
| *G16H 70/60* | (2018.01) |
| *G16H 10/40* | (2018.01) |
| *G16H 50/20* | (2018.01) |
| *G16H 30/40* | (2018.01) |
| *G06K 9/62* | (2022.01) |
| *G06T 7/00* | (2017.01) |

(52) U.S. Cl.
CPC ............... *G06N 3/04* (2013.01); *G06N 3/08* (2013.01); *G06T 7/0012* (2013.01); *G06T 7/11* (2017.01); *G06V 20/698* (2022.01); *G16H 10/40* (2018.01); *G16H 30/40* (2018.01); *G16H 50/20* (2018.01); *G16H 70/60* (2018.01); *G06T 2207/20081* (2013.01); *G06T 2207/20084* (2013.01); *G06T 2207/30024* (2013.01)

(58) Field of Classification Search
CPC ...... G06K 9/6256; G06K 9/627; G06K 9/628; G06K 9/6272; G06N 3/04; G06N 3/08; G06T 7/0012; G06T 7/11; G06T 2207/10064; G06T 2207/20021; G06T 2207/20084; G06T 2207/30024; G16H 10/40; G16H 30/40; G16H 50/20; G16H 70/60

See application file for complete search history.

(56) References Cited

U.S. PATENT DOCUMENTS

| | | | |
|---|---|---|---|
| 2017/0124432 | A1 | 5/2017 | Chen et al. |
| 2019/0286880 | A1 | 9/2019 | Jackson et al. |
| 2019/0325621 | A1 | 10/2019 | Wang et al. |
| 2019/0347847 | A1 | 11/2019 | Elgharib et al. |
| 2020/0058126 | A1 | 2/2020 | Wang et al. |
| 2020/0129263 | A1 | 4/2020 | Izadyyazdanabadi et al. |
| 2020/0160032 | A1* | 5/2020 | Allen .................. G06T 7/0012 |
| 2020/0167972 | A1 | 5/2020 | Birnhack et al. |
| 2020/0226422 | A1 | 7/2020 | Li et al. |
| 2020/0272864 | A1 | 8/2020 | Faust et al. |
| 2020/0294231 | A1* | 9/2020 | Tosun .................. G06K 9/6263 |
| 2020/0388029 | A1* | 12/2020 | Saltz .................. G06K 9/6267 |
| 2020/0388033 | A1 | 12/2020 | Matlock et al. |
| 2021/0027098 | A1 | 1/2021 | Ge et al. |
| 2021/0043331 | A1 | 2/2021 | Ozcan et al. |
| 2021/0089744 | A1 | 3/2021 | Ianni et al. |
| 2021/0217212 | A1 | 7/2021 | Birnhack et al. |

FOREIGN PATENT DOCUMENTS

| | | |
|---|---|---|
| WO | 2020/014477 A1 | 1/2020 |
| WO | 2020/182710 A1 | 9/2020 |
| WO | 2020/193708 A1 | 10/2020 |
| WO | 2020/229585 A1 | 11/2020 |
| WO | 2022/061083 A1 | 3/2022 |
| WO | 2022/066725 A1 | 3/2022 |
| WO | 2022/066736 A1 | 3/2022 |

OTHER PUBLICATIONS

Ji, J., "Gradient-based Interpretation on Convolutional Neural Network for Classification of Pathological Images," 2019 International Conference on Information Technology and Computer Application (ITCA), IEEE, 2019, pp. 83-86 (retrieved from the internet on Nov. 21, 2021), <URL: https://ieeexplore.IEEE.org/stamp/stamp.jsp?p=&arnumber=9092504>.

International Search Report and Written Opinion of the International Searching Authority dated Dec. 22, 2021 in International Apln. No. PCT/US2021/051495, 8 pages.

International Search Report and Written Opinion of the International Searching Authority dated Dec. 17, 2021 in International Apln. No. PCT/US2021/050828, 10 pages.

International Search Report and Written Opinion of the International Searching Authority dated Dec. 27, 2021 in International Apln. No. PCT/US2021/051506, 9 pages.

Samsi, S., et al., "Colorization of H&E stained tissue using Deep Learning," 2018 40th Annual International Conference of the IEEE Engineering in Medicine and Biology Society (EMBC), IEEE, 2018, pp. 640-643.

Tellez, D., et al., "Quantifying the effects of data augmentation and stain color normalization in convolutional neural networks for computational pathology," arXiv:1902.06543v1 [cs.CV], Feb. 18, 2019, pp. 1-12.

Extended European Search Report dated Feb. 12, 2021 in European Apln. No. 20197904 4, 8 pages.

Yuan, E., et al., "Neural Stain Normalization and Unsupervised Classification of Cell Nuclei in Histopathological Breast Cancer Images," arXiv:1811.03815v1 [cs.CV], Nov. 9, 2018, pp. 1-9.

Zhang, R., et al., "Colorful Image Colorization," arXiv: 1603.08511v5 [cs.CV], Oct. 5, 2016, pp. 1-29.

Gal et al., "Dropout as a Bayesian Approximation: Representing Model Uncertainty in Deep Learning," Proceedings of the 33rd International Conference on Machine Learning, vol. 48, 2016, 10 pages.

* cited by examiner

AUTOMATED WHOLE-SLIDE IMAGE CLASSIFICATION USING DEEP LEARNING

RELATED APPLICATIONS

This application claims priority to, and the benefit of, both U.S. Provisional Patent Application No. 62/904,146 entitled "Automated Whole-Slide Image Classification Using Deep Learning" filed Sep. 23, 2020, and U.S. Provisional Patent Application No. 62/904,263 entitled "Stain Normalization for Automated Whole-Slide Image Classification" filed Sep. 23, 2020, which are both hereby incorporated by reference in their entireties.

FIELD

This disclosure relates generally to pathology.

BACKGROUND

Every year in the United States, twelve million skin lesions are biopsied, with over five million new skin cancer cases diagnosed. After a skin tissue specimen is biopsied, the tissue is fixed, embedded, sectioned, and stained with hematoxylin and eosin (H&E) on (one or several) glass slides, ultimately to be examined under microscope by a dermatologist, general pathologist, or dermatopathologist who provides a diagnosis for each tissue specimen. Owing to the large variety of over 500 distinct skin pathologies and the severe consequences of a critical misdiagnosis, diagnosis in dermatopathology demands specialized training and education. Although inter-observer concordance in dermatopathology is estimated between 90% and 95%, there are some distinctions that present frequent disagreement among pathologists, such as in the case of melanoma vs. benign melanocytic nevi. However, even when diagnosis is accurate, the process can be made more efficient by reducing the turnaround time for each case and by improving pathologist workload distribution. Often, cases get first sent to a generalist—sometimes a dermatologist who diagnoses specimens biopsied in their clinical practice. Only if the diagnosis is not a straightforward one is it sent to a specialist to diagnose. This can result in a delay of days to the patient receiving a diagnosis in sometimes-critical cases. The rise in adoption of digital pathology provides an opportunity for the use of deep learning-based methods for closing these gaps in diagnostic reliability and efficiency.

In recent years, attempts have been made to use deep neural networks for identifying diagnostically relevant patterns in radiology and pathology images. While some attempts appear worth pursuing, the translation of such methods to digital pathology is non-trivial. Among the reasons for this is sheer image size; a whole slide image can contain several gigabytes of image data and billions of pixels. Additionally, non-standardized image appearance (variability in tissue preparation, staining, scanned appearance, presence of artifacts) and the number of pathologic abnormalities that can be observed present unique barriers to development of deployable deep learning applications in pathology. For example, it is known that inter-site variance—in the form of stain and other image properties—can have a strong impact on deep learning models. Nonetheless, deep learning-based methods have recently shown promise in segmentation tasks which can be used to compute features for traditional classifiers, and more recently for some classification tasks. However, many focus only on a single diagnostic class to make binary classifications whose utility breaks down when there is more than one relevant pathology of interest. Additionally, many of these methods have focused on curated datasets consisting of fewer than five pathologies with little diagnostic and image variability.

The insufficiency of known models developed and tested using small curated datasets such as CAMELYON30 has been effectively demonstrated. See Campanella, G. et al., *Clinical-grade computational pathology using weakly supervised deep learning on whole slide images*, Nature Medicine 1 (2019), hereinafter, "Campanella". However, while claiming to validate on data free of curation, their dataset features limited capture of not only biological variability (e.g., ignores commonly occurring prostatic intraepithelial neoplasia and atypical glandular structures) but also technical variability originating from slide preparation and scanning characteristics (resulting in exclusion of slides with pen markings, need for retrospective human correction of select results, and poorer performance on externally-scanned images). In contrast to these deep learning systems exposed to contrived pathology problems and datasets, human pathologists are trained to recognize hundreds of morphological variants of diseases they are likely to encounter in their careers and must adapt to variations in tissue preparation and staining protocols. Deep learning algorithms can also be sensitive to image artifacts, in addition to these variations. Some have attempted to account for these issues by detecting and pre-screening image artifacts, either by automatically or manually removing slides with artifacts. Campanella et. al include variability in nonexcluded artifacts which others lack, but still selectively exclude images with ink markings, which have been shown to affect predictions of neural networks.

In addition to the problems identified above regarding automated pathology, problems exist in training and using classifiers due to variations among whole slide images produced by various labs. Because the appearance of a whole slide image varies from lab to lab, scanner to scanner, with the same scanner over time, and even varies based on the brand of stain used, images acquired from different labs or scanners are not effectively interpretable by a model which is trained on the variations of a single lab or image appearance. To the trained human eye, stain differences may be the most dramatic differences between different labs' images. Therefore, much of the work in the field so far has focused on normalizing stain. Typically, stain normalization attempts to extract the two main components of the image color which come from the hematoxylin (H) and eosin (E) stains. There are many methods of stain normalization, and most of the previous gold standard methods have not used any form of deep learning. They typically require a target image, extract the components of that image, and apply a transform computed between those and the components of the image to be normalized. This has several disadvantages:

1. It requires a target or reference image, which is a single example which should represent the "ideal" stain. It is difficult to select an image which has some "ideal" stain properties, and yet exhibits enough variation in tissue types to be useful for comparing images.

2. Methods like Vahadane stain normalization are highly sensitive to the target image, as well as to any background or atypically-colored regions included in either the target or to-be-normalized image. It is therefore easy to get an erroneous/improbable stain normalization result, or one that is not representative.

3. As a result of the above, similar images, e.g., those from slightly separated slices of tissue, will produce inconsistent normalized stain results, which is very problematic when training a model to classify a pathology.

In addition to just changes in the color or stain of the images when compared between labs, other changes in image appearance between labs may be present. Some images had more or less noise, differences in brightness and contrast, hue and saturation, or orientation of the tissue on the slide. While minor changes in these variables might not affect a human's ability to diagnose a case from the images very much, these factors can be important to a deep learning system's ability to correctly identify pathology. There are not currently any methods of correcting for any of these factors in terms of pre-processing images to be assessed by a deep learning system.

SUMMARY

According to various embodiments, computer-implemented method of classifying a tissue specimen is presented. The method includes obtaining a computer readable image of the tissue specimen; segmenting the image into a first plurality of segments; selecting, from among the first plurality of segments, a second plurality of segments that include at least one region of interest; applying, to the second plurality of segments, an electronic convolutional neural network trained by a training corpus including a set of pluralities of tissue sample image segments, each of the pluralities of tissue sample image segments including image segments from within a same tissue sample image, each of the pluralities of tissue sample image segments labeled according to one of a plurality of primary pathology classes, wherein the plurality of primary pathology classes consist of a plurality of majority primary pathology classes, wherein the plurality of majority primary pathology classes collectively include a majority of pathologies of a particular tissue type according to prevalence, and a class for tissue sample image segments not in the plurality of majority primary pathology classes, such that a primary pathology classification is output; and providing the primary pathology classification.

Various optional features of the above embodiments include the following. The method may include applying, to at least a portion of the second plurality of segments, a trained classifier trained by a training corpus including a set of secondary pluralities of tissue sample image segments, each set of secondary pluralities including image segments from within a same tissue sample image, each set of secondary pluralities labeled according to some pathology subclass within the primary pathology classification, such that a secondary pathology classification is output; and providing the secondary pathology classification. The primary pathology classification may be provided to at least one of: a clinical workflow, a laboratory information system, or a report generation system. The plurality of majority primary pathology classes may include at least one of: basaloid patterns class, squamous patterns class, or melanocytic patterns class. The class for tissue sample image segments not in the plurality of majority primary pathology classes may include tissue sample image segments for at least one of: ulcerations, epidermal inclusion cysts, or scars. The applying, to the second plurality of segments, the electronic convolutional neural network may include: applying, to the second plurality of segments, the electronic convolutional neural network a plurality of times, each time using a different proper subset of neurons in the electronic convolutional neural network, such that a plurality of predictions within each of the primary pathology classes are produced; combining, within each of the primary pathology classes, a respective plurality of predictions, such that a combined prediction for each of the primary pathology classes is produced; and selecting a main combined prediction as the primary pathology classification. Each different proper subset of neurons in the electronic convolutional neural network may consist of less than or equal to a selected value of between 50% and 99% of neurons in the electronic convolutional neural network. The plurality of times may include a number of times selected from the range from 10 times to 100 times. The combining, within each of the primary pathology classes, the respective plurality of predictions, may include determining a mean of sigmoid function outputs for respective pluralities of predictions within each of the primary pathology classes; and the selecting the main combined prediction may include selecting a maximum mean. The method may further include determining that the maximum mean exceeds a threshold value, wherein the threshold value represents a mean of sigmoid function outputs, for a plurality of validation images of tissue specimens with known diagnoses according to the plurality of primary pathology classes, corresponding to a selected confidence level.

According to various embodiments, a system for classifying a tissue specimen is presented. The system includes at least one electronic processor and at least one persistent electronic memory communicatively coupled to the at least one electronic processor, the at least one persistent memory including computer readable instructions that, when executed by the at least one electronic processor, configure the at least one electronic processor to perform operations including: obtaining a computer readable image of the tissue specimen; segmenting the image into a first plurality of segments; selecting, from among the first plurality of segments, a second plurality of segments that include at least one region of interest; applying, to the second plurality of segments, an electronic convolutional neural network trained by a training corpus including a set of pluralities of tissue sample image segments, each of the pluralities of tissue sample image segments including image segments from within a same tissue sample image, each of the pluralities of tissue sample image segments labeled according to one of a plurality of primary pathology classes, wherein the plurality of primary pathology classes consist of a plurality of majority primary pathology classes, wherein the plurality of majority primary pathology classes collectively include a majority of pathologies of a particular tissue type according to prevalence, and a class for tissue sample image segments not in the plurality of majority primary pathology classes, such that a primary pathology classification is output; and providing the primary pathology classification.

various optional features of the above embodiments include the following. The operations may further include: applying, to at least a portion of the second plurality of segments, a trained classifier trained by a training corpus including a set of secondary pluralities of tissue sample image segments, each set of secondary pluralities including image segments from within a same tissue sample image, each set of secondary pluralities labeled according to some pathology subclass within the primary pathology classification, such that a secondary pathology classification is output; and providing the secondary pathology classification. The primary pathology classification may be provided to at least one of: a clinical workflow, a laboratory information system, or a report generation system. The plurality of majority primary pathology classes may include at least one of:

basaloid patterns class, squamous patterns class, or melanocytic patterns class. The class for tissue sample image segments not in the plurality of majority primary pathology classes may include tissue sample image segments for at least one of: ulcerations, epidermal inclusion cysts, or scars. The applying, to the second plurality of segments, the electronic convolutional neural network may include: applying, to the second plurality of segments, the electronic convolutional neural network a plurality of times, each time using a different proper subset of neurons in the electronic convolutional neural network, such that a plurality of predictions within each of the primary pathology classes are produced; combining, within each of the primary pathology classes, a respective plurality of predictions, such that a combined prediction for each of the primary pathology classes is produced; and selecting a main combined prediction as the primary pathology classification. Each different proper subset of neurons in the electronic convolutional neural network may consist of less than or equal to a selected value of between 50% and 99% of neurons in the electronic convolutional neural network. The plurality of times may include a number of times selected from the range from 10 times to 100 times. The combining, within each of the primary pathology classes, the respective plurality of predictions, may include determining a mean of sigmoid function outputs for respective pluralities of predictions within each of the primary pathology classes; and wherein the selecting the main combined prediction may include selecting a maximum mean. The operations may further include determining that the maximum mean exceeds a threshold value, wherein the threshold value represents a mean of sigmoid function outputs, for a plurality of validation images of tissue specimens with known diagnoses according to the plurality of primary pathology classes, corresponding to a selected confidence level.

BRIEF DESCRIPTION OF THE DRAWINGS

Various features of the embodiments can be more fully appreciated, as the same become better understood with reference to the following detailed description of the embodiments when considered in connection with the accompanying figures, in which.

DESCRIPTION OF THE EMBODIMENTS

Figure 1:
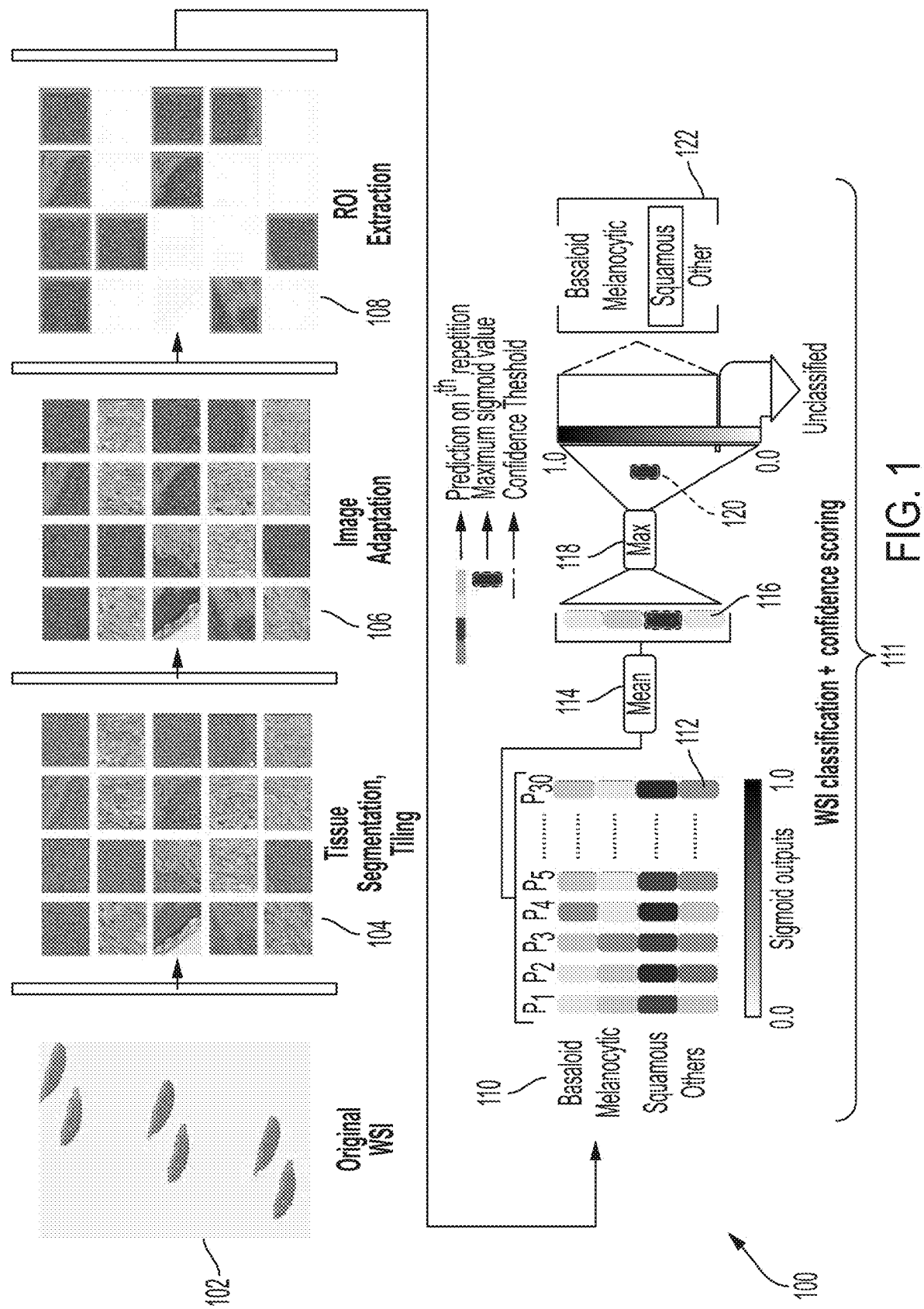
FIG. 1 is a schematic diagram of a system for classifying a whole slide image using a deep learning classifier according to various embodiments.

Reference will now be made in detail to example implementations, illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

This description includes two main parts. Part I discloses techniques for automated whole slide image classification using deep learning, including techniques for determining an optional threshold corresponding to a confidence level. Part II discloses techniques for stain normalization. The techniques of Part I may be used with or without the techniques of Part II, and the techniques of Part II may be used in the context of the techniques of Part I or independently.

I. Automated Whole Slide Image Classification Using Deep Learning

A. Introduction

A real-world deep learning pathology system should be demonstrably robust to the variations noted by Campanella as described above in the Background. It should be tested on non-selected specimens, with no exclusions and no pre-screening or post-screening. A comprehensive test set for robustly assessing system performance should contain:

1. Image from multiple labs, with markedly varied stain and image appearance due to scanning using different models and vendors, and different tissue preparation and staining protocols;

2. Image wholly representative of a diagnostic workload in the subspecialty (i.e., not excluding pathologic or morphologic variations which occur in a sampled time-period);

3. Image with a host of naturally-occurring and human-induced artifacts: scratches, tissue fixation artifacts, air bubbles, dust and dirt, smudges, out-of-focus or blurred regions, scanner-induced misregistrations, striping, pen ink or letters on slides, inked tissue margins, patching errors, noise, color/calibration/light variations, knife-edge artifacts, tissue folds, and lack of tissue present; and 4. (In some instances) images with no visible pathology, or with no conclusive diagnosis, covering the breadth of cases occurring in diagnostic practice This disclosure presents a pathology deep learning system (PDLS) that is capable of classifying whole slide images containing H&E-stained and prepped skin biopsy or re-excised tissue into one of four diagnostically-relevant classes based on tissue appearance. Some embodiments return a measure of confidence in the model's assessment; this is useful in such classifications because of the wide range of variability in the data. A lab-ready system should be able to not only return accurate predictions for commonly occurring pathologies and image appearances, but also flag the significant remainder of images whose unusual features lie outside the range allowing reliable model prediction.

A reduction to practice was developed on a whole slide image from a single lab and independently tested on a completely uncurated and unrefined set of 13,537 sequentially accessioned H&E-stained images from three additional labs, each using a different scanner and different staining and preparation protocol. No images were excluded. To the inventors' knowledge, this test set is the largest in pathology to date. The reduction to practice satisfied all the criteria listed above for real-world assessment, and is therefore, to the inventors' knowledge, the first truly real-world-validated deep learning system in pathology.

B. Whole Slide Image Classification

Some embodiments provide a computer-implemented system for, and method of, classifying a tissue specimen. The tissue specimen may be human tissue, such as by way of non-limiting example, a human cutaneous tissue sample. Embodiments may include obtaining a computer readable image of the tissues specimen, e.g., on a computer readable medium, over a network such as the internet, or from digitizing a whole slide image. Embodiments may segment the image into a first plurality of segments, e.g., using computer vision such as Otsu's thresholding or using a convolutional neural network. Next, embodiments may optionally perform stain normalization and image adaptation on the image, e.g., using CNN-1 (106) as described in detail below in reference to FIG. 1. Embodiments may then select, from among the first plurality of segments, a second plurality of segments that include at least one region of interest, e.g., using CNN-2 (108) as described in detail below in reference to FIG. 1. Embodiments may then apply, to the second plurality of segments, an electronic convolutional neural network trained by a training corpus comprising a set of pluralities of tissue sample image segments, each of the pluralities of tissue sample image segments comprising image segments from within a same tissue sample image, each of the pluralities of tissue sample image segments labeled according to one of a plurality of primary pathology classes, where the plurality of primary pathology classes consist of a plurality of majority primary pathology classes, where the plurality of primary pathology classes collectively comprise a majority of pathologies of a particular tissue type according to prevalence, and a class for tissue sample image segments not in the plurality of majority primary pathology classes, such that a classification primary pathology class is output. Embodiments may utilize CNN-3 (111) as described in detail below to in reference to FIG. 1 to that end. Embodiments may then provide the classification primary pathology class, e.g., by displaying on a computer monitor or sending a message such as an email. Example embodiments are described in detail presently.

FIG. 1 is a schematic diagram of a system 100 for classifying a whole slide image using a deep learning classifier according to various embodiments. System 100 takes as input whole slide image 102 and classifies it using a cascade of three independently-trained convolutional neural networks, CNN-1 (106), CNN-2 (108), and CNN-3 (111) as follows. CNN-1 (106) adapts the image appearance to a common feature domain, accounting for variations in stain and appearance. CNN-2 (108) identifies regions of interest (ROI) for further processing. The final network, CNN-3 (111), classifies the whole slide image into one of four classes defined broadly by their histologic characteristics: basaloid, melanocytic, squamous, or other, as further described below. Though the classifier operates at the level of an individual whole slide image, some specimens are spread across multiple whole slide images, and therefore these decisions may be aggregated to the specimen-level. According to some embodiments, CNN-3 (111) is trained such that each image result returns a predicted confidence in the accuracy of the outcome, along with predicted class. This allows discarding predictions that are determined by such embodiments as likely to be false.

An example process for classifying a whole slide image with the deep learning system is described presently with respect to FIG. 1. In brief, an input whole slide image 102 is first divided into tissue patches according to a tiling procedure 104; those patches pass through CNN-1 (106) which adapts their stain and appearance to the target domain; they then pass through CNN-2 (108) which identifies the regions of interest (patches) to pass to CNN-3 (111), which performs a four-way classification, and repeats this multiple times to yield multiple predictions. These predictions are then converted into an output classification into one of the four classes. Further processing may be performed in order to more finely classify the whole slide image within its classification class. The convolutional neural networks of system 100 are discussed in detail presently.

Because system 100 may be trained only on a single lab's data, implementations may first perform image adaptation to adapt images received from test labs to a domain where the image features are interpretable by system 100. Without adaptation, unaccounted-for variations in the images due to staining and scanning protocols can adversely affect the performance of convolutional neural networks. In system 100, image adaptation is shown as being performed using CNN-1 (106), which takes as input an image tile of whole slide image 102 and outputs an adapted tile of the same size and shape but with standardized image appearance. In the reduction to practice, CNN-1 (106) was trained using 300,000 tiles from the Reference Lab, to mimic the average image appearance from the Reference Lab when given an input tile.

Subsequently, region of interest extraction is performed using CNN-2 (108). This convolutional neural network may be trained using expert annotations by a dermatopathologist as the ground truth. It may be trained to segment regions exhibiting abnormal features indicative of pathology. The model takes input of a single tile and outputs a segmentation map. Tiles may be selected corresponding to the positive regions of the segmentation map; set all identified tiles of interest, t is passed on to the final stage classifier.

The final whole slide image classification is then performed using CNN-3 (111), which predicts a label/for the set of tiles t identified by CNN-2 (108), where:

l∈{Basaloid; Squamous; Melanocytic; Others}

The design of target classes 110 may be based on the prevalence of each class's constituent pathologies and the presence of visually-similar and histologically-similar class representative features. Such a prevalence may be a prevalence in the general population. For example, embodiments may perform classification of whole slide images into four classes 110: Basaloid, Squamous, Melanocytic, and Others. These four classes 110 may be defined by the following histological descriptions of their features:

1. Basaloid: Abnormal proliferations of basaloid-oval cells having scant cytoplasm and focal hyperchromasia of nuclei; cells in islands of variable size with round, broad-based and angular morphologies; peripheral palisading of nuclei, peritumoral clefting, and a fibromyxoid stroma.

2. Squamous: Squamoid epithelial proliferations ranging from a hyperplastic, papillomatous and thickened spinous layer to focal and full thickness atypia of the spinous zone as well as invasive strands of atypical epithelium extending into the dermis at various levels.

3. Melanocytic: Cells of melanocytic origin in the dermis, in symmetric nested and diffuse aggregates and within the intraepidermal compartment as single cell melanocytes and nests of melanocytes. Nests may be variable in size, irregularly spaced, and single cell melanocytes may be solitary, confluent, hyperchromatic, pagetoid and with pagetoid spread into the epidermis. Cellular atypia can range from none to striking anaplasia and may be in situ or invasive.

4. Other. Morphologic and histologic patterns that include either the absence of a specific abnormality or one of a wide variety of other neoplastic and inflammatory disorders which are both epithelial and dermal in location and etiology, and which are confidently classified as not belonging to classes 1-3.

These four classes 110 account for more than 200 pathologic entities in the reduction to practice training set, and their mapping to the most prevalent pathologic entities in the training set is illustrated below in FIG. 3.

Based on these classes, CNN-3 (111) performs a four-way classification into classes 110, and repeats this multiple (e.g., thirty) times to yield multiple predictions, where each prediction $P_i$ may be represented as a vector (e.g., vector 112) of dimension $N_{classes}=4$. Each prediction may be performed using a randomly selected subset of neurons of CNN-3 (111), e.g., 70% of the full set. A mean operation 114 is applied class-wise to obtain class mean vector 116, which includes means of the sigmoid outputs for each class. A maximum operation 118 is then applied to class mean vector 116, which identifies the max 120 of the class. The max 120 of the mean 116 of sigmoid output is used for both the prediction and optionally for a confidence score (described below in detail in Section I(C)). If the confidence score surpasses a pre-defined threshold, the corresponding class decision 122 is assigned.

Diagnostic labels may be reported at the level of a specimen, which may be represented by one or several whole slide images. Therefore, the predictions of system 100 may be aggregated across whole slide images to the specimen level; this is accomplished by assigning to a given specimen the maximum-confidence prediction across all whole slide images representing that specimen.

In the reduction to practice introduced at the end of Section I(A), the training data for system 100 was developed using H&E-stained whole slide images from Dermatopathology Laboratory of Central States (DLCS), which is referred to as the "Reference Lab" herein. This dataset is made up of two subsets, the first (3,070 whole slide images) consisting of images representing commonly diagnosed pathologic entities, and the second (2,000 whole slide images) consisting of all cases accessioned during a discrete period of time, representing the typical distribution seen by the lab. This combined Reference Lab set of 5,070 whole slide images was partitioned randomly into training (70%), validation (15%), and testing (15%) sets, such that whole slide images from any given specimen are not split between sets.

To demonstrate its robustness to variations in scanners, staining, and image acquisition protocols, the reduction to practice was also tested on 13,537 whole slide images collected from three of the largest-volume dermatopathology labs in the United States (referred to as "Test Labs"). Each Test Lab selected a date range within the past four years (based on slide availability) from which to scan a sequentially accessioned set of approximately 5,000 slides. All parameters and stages of the reduction to practice pipeline were held fixed after development on the Reference Lab, with the exception of CNN-3 (111), whose weights were fine-tuned independently using the 520-image calibration set of each lab. (This process is referred to herein as "calibration".) The calibration set for each consisted of the first 500 whole slide images supplemented by twenty additional whole slide images from melanoma specimens. 80% of the 520 images were used for fine-tuning, and 20% for lab-specific validation of the fine-tuning and image adaptation procedures. Specimens from the same patient were not split between fine-tuning, validation and test sets. Each of the three Test Labs scanned their slides using a different scanner vendor and model. After this calibration, all parameters were permanently held fixed, and the system was run only once on each lab's test set of approximately 4,500 whole slide images (range 4451 to 4585) for 13,537 in total.

Results are reported for the test set, consisting of 13,537 whole slide images from the three test labs which were not used in model training or development. The reduction to practice effectively classified whole slide images into the four classes with an overall accuracy of 78% before thresholding on confidence score. Importantly, in specimens whose predictions exceeded the confidence threshold, the reduction to practice achieved an accuracy of 83%, 94%, and 98% for Confidence Levels 1, 2 and 3, respectively. Further discussion of the performance of the reduction to practice follows immediately below in reference to FIG. 2.

Figure 2:
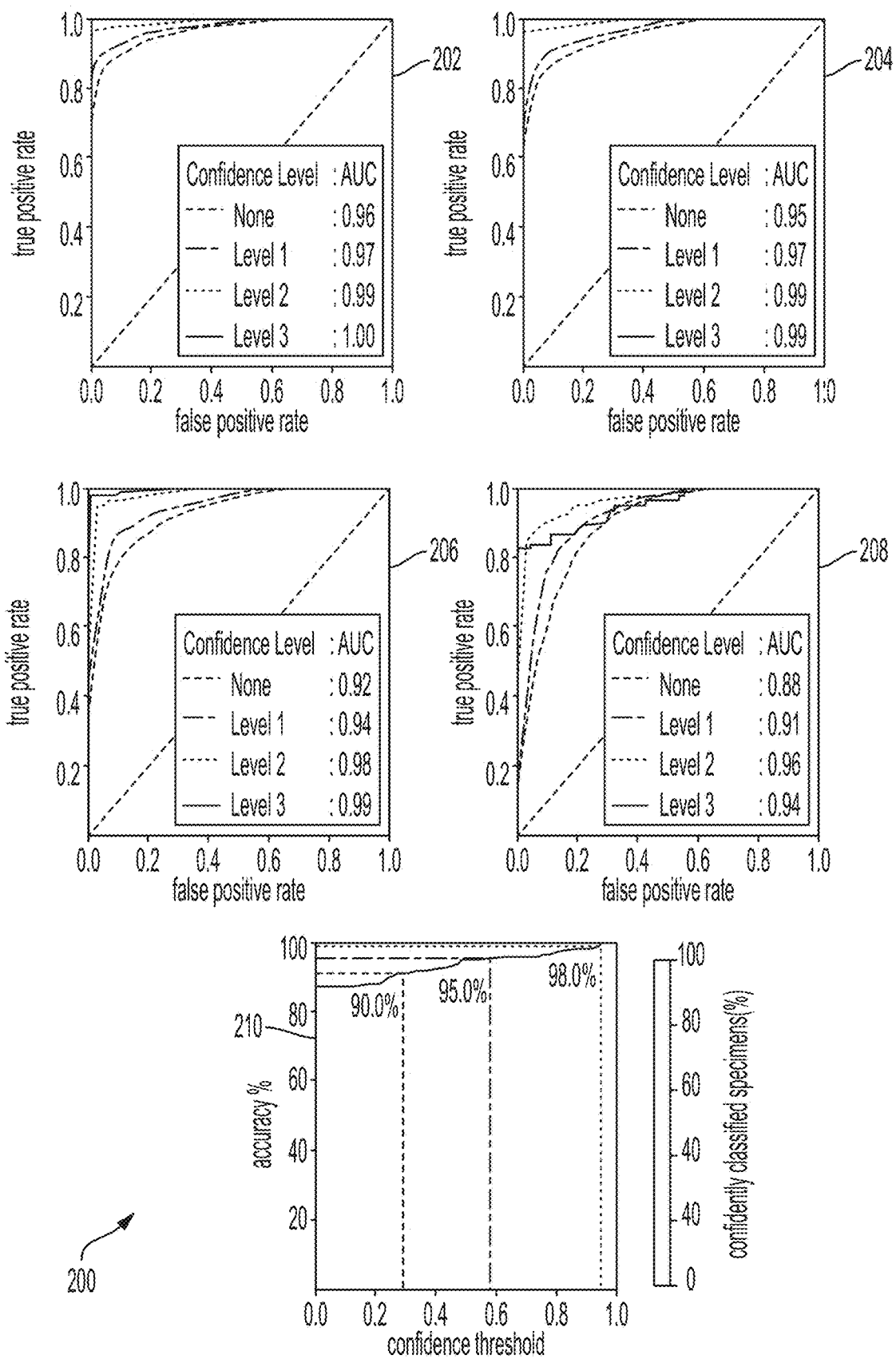
FIG. 2 depicts receiver operating curves by lab, class, and confidence according to an example reduction to practice.
Figure 2:
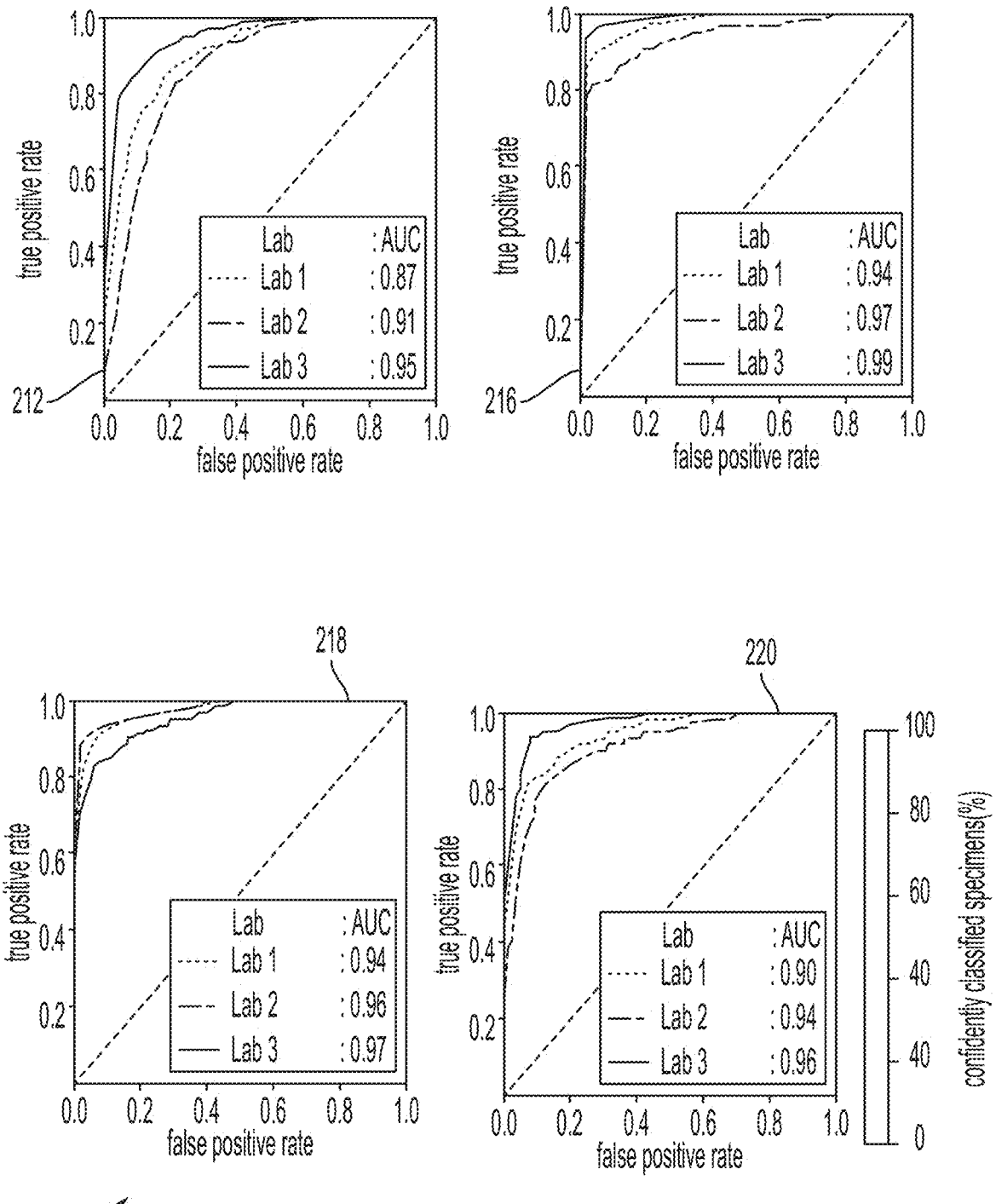

FIG. 2 depicts receiver operating curves 202, 204, 206, 208, 210, 212, 214, 216, 281 by lab, class, and confidence for the test set of 13,537 images according to the example reduction to practice. ROC curves are shown for basaloid (202, 212), melanocytic (204, 216), squamous (206, 218) and other (208, 220) classes, with percentage of specimens classified for each curve represented by the shading bar at right. The four curves (202, 204, 206, 208) represent the respective thresholded confidence levels or no confidence threshold ("None"). As confidence level increases, a larger number of images do not meet the threshold and are excluded from the analysis, as indicated by the shading. At Levels, 1, 2, and 3, the percentage of test specimens exceeding the confidence threshold was 83%, 46% and 20%, respectively. Area under the curve (AUC) increased with increasing confidence level. Similar results are shown for Level 1 for the test labs; the four curves in (212, 216, 218, 220) represent each of the three labs. In curve 210, validation set accuracy in the Reference Lab is plotted versus sigmoid confidence score, with dashed lines corresponding to the sigmoid confidence thresholds set (and fixed) at 90% (Level 1), 95% (Level 2), and 98% (Level 3). Curve 210 depicts empirical overall accuracy according to confidence threshold.

Figure 3:
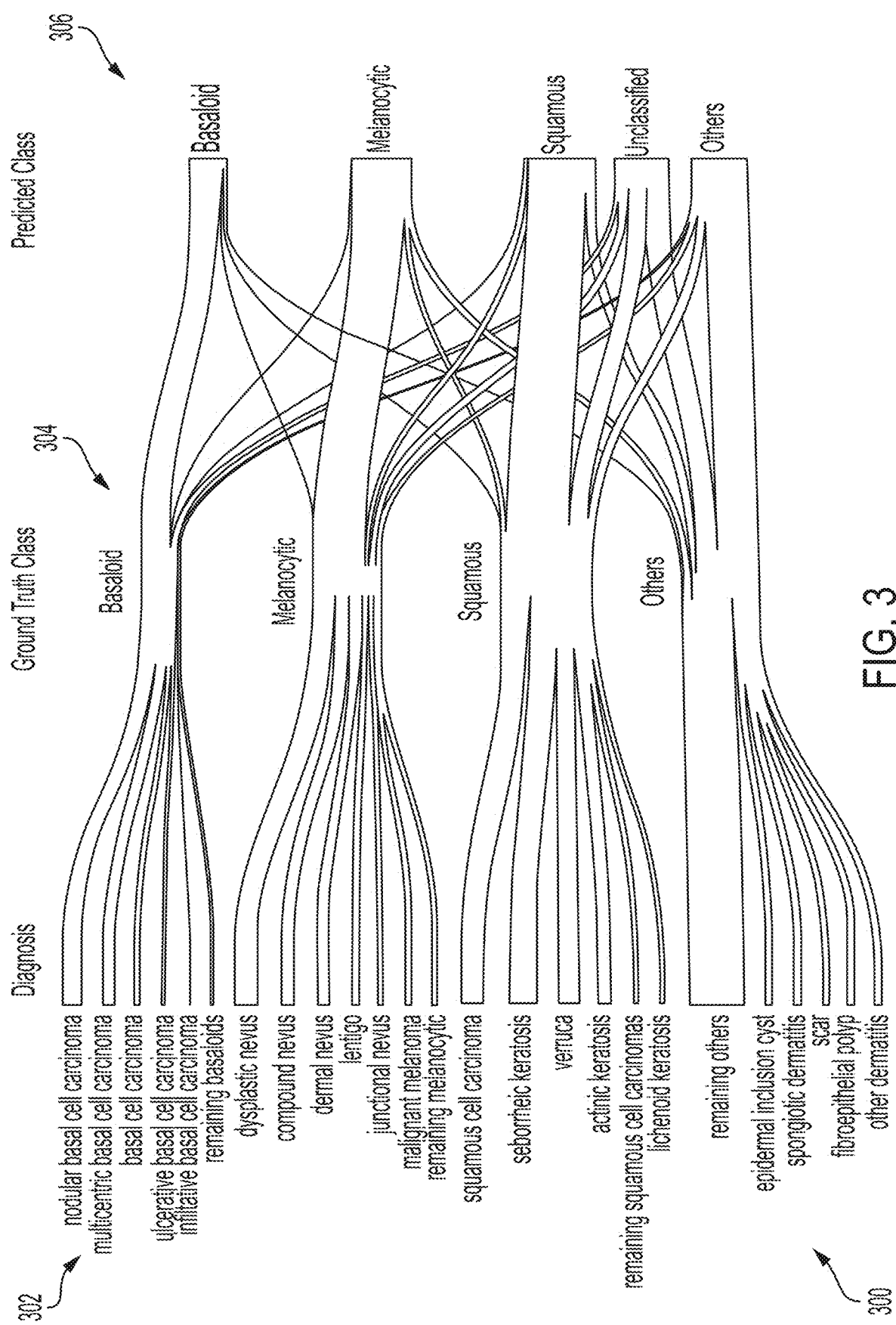
FIG. 3 depicts a Sankey diagram depicting how ground truth classes map to the top five most common diagnoses according to various embodiments.

FIG. 3 depicts a Sankey diagram 300 depicting how ground truth classes 302 map to the top five most common diagnoses 306 according to various embodiments. That is, FIG. 3 shows the mapping of ground truth class 304 to the proportion correctly predicted 306 as well as proportions confused for each of the other classes or remaining unclassified (at Level 1) due to lack of a confident prediction or absence of any ROI detected by CNN-2 (106). FIG. 3 thus depicts the proportion of images correctly classified, along with distribution of misclassifications and unclassified specimens at confidence Level 1 (306). The width of each bar is proportional to the corresponding number of specimens in the three-lab test set. Additionally FIG. 3 shows the most common ground-truth diagnoses 302 in each of the four classes 304.

Figure 4:
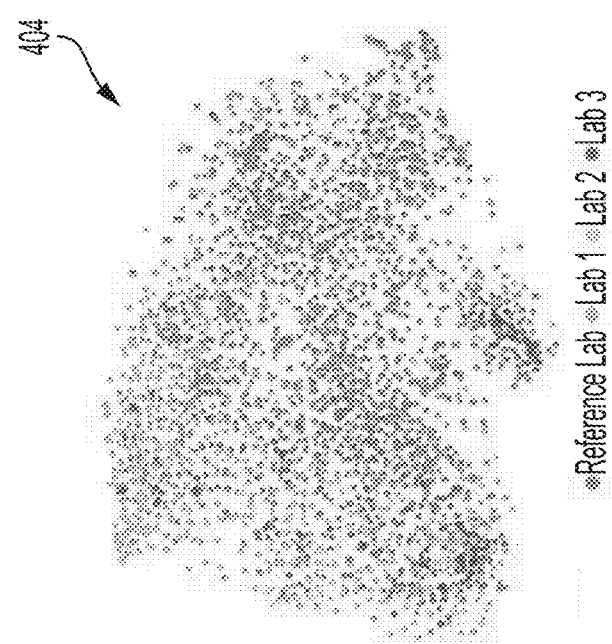
FIG. 4 depicts image feature vectors in two-dimensional t-distributed stochastic neighbor (t-SNE) embedded plots according to an example reduction to practice.
Figure 4:
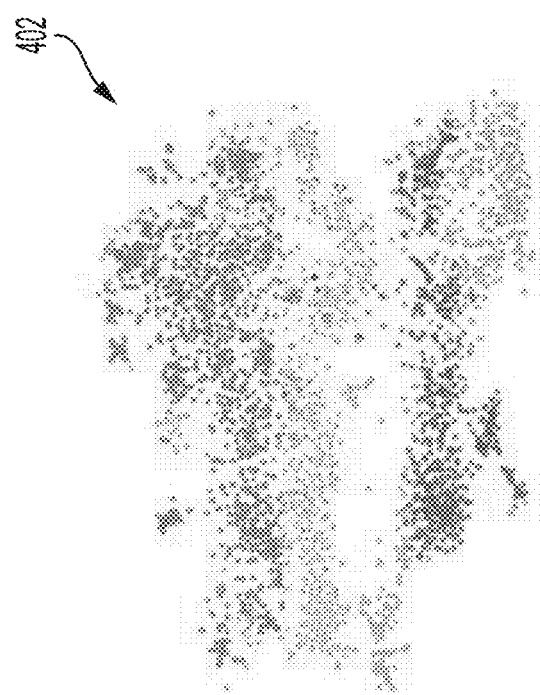
Figure 4:
Figure 4:

FIG. 4 depicts image feature vectors in two-dimensional t-distributed stochastic neighbor (t-SNE) embedded plots 402, 404, 406, 408, 410, 412 for the reduction to practice. To demonstrate that the image adaptation performed by CNN-1 (106) effectively reduces inter-site differences, the inventors used t-distributed stochastic neighbor embedding (t-SNE) to compare the feature space computed by CNN-2 (108) with and without first performing the image adaptation. In FIG. 4, plot 402 depicts the embedded feature space of CNN-2 (108) without first performing image adaptation, and plot 404 depicts the embedded feature space from CNN-2 (108) when image adaptation is performed first. Each point represents an image patch within a whole-slide image, colored by lab.

The bottom row of plots in FIG. 4 depicts feature embeddings from CNN-3 (111), where each point represents a single whole slide image and is colored according to ground-truth classification. Thus, t-SNE as depicted in FIG. 4 shows the internal feature representation learned by the final classifier, CNN-3 (111), in plot 406. All images are classified at baseline plot 406, where plots 408, 410, 412 show increasing confidence thresholds (plot 408 for Level 1, plot 410 for Level 2, and plot 412 for Level 3), with images not meeting the threshold depicted lighter. The clustering shows strong class separation between the four classes, with stronger separation and fewer whole slide images classified as confidence level increases.

Figure 5:
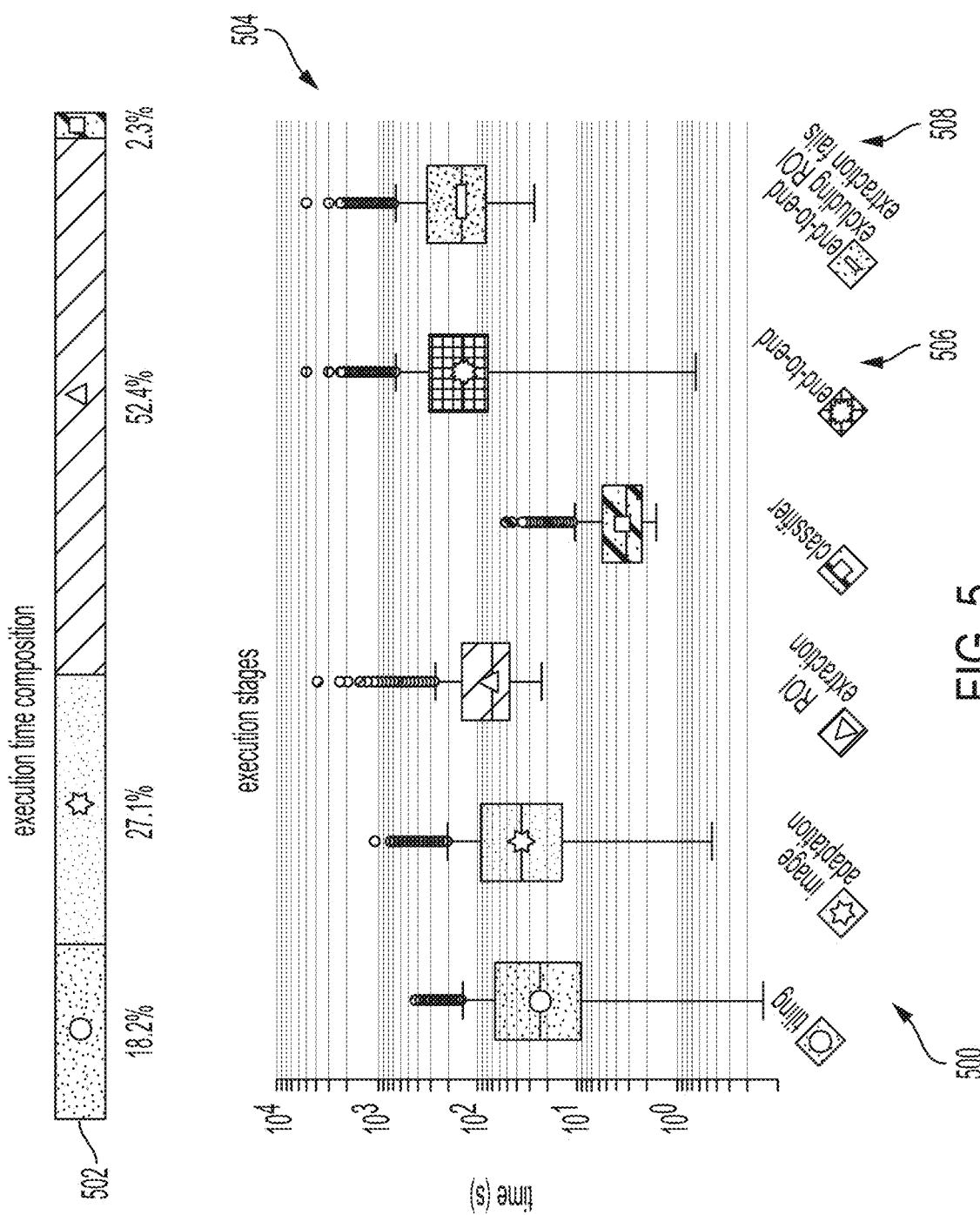
FIG. 5 depicts execution times per whole slide image, computed in a set of 1,536 whole slide images from three test labs.

FIG. 5 depicts execution times per whole slide image, computed in a set of 1,536 whole slide images from three test labs. The median percentage of total execution time for each stage of the deep learning system is shown at 502. A boxplot of the execution time required at each stage of the pipeline is shown at 504, along with total end-to-end execution time for all images (506), and excluding images for which no regions of interest are detected (508).

Compute time profiling was performed on an AmazonWeb Services EC2 P3.8x large instance equipped with 32 core Intel Xeon E5-2686 processors, 244 GB RAM, and four 16 GB NVIDIA Tesla v100 GPUs supported by NVLink for peer-to-peer GPU communication. Compute time was measured on the calibration sets of each of the test labs, in total 1536 whole slide images.

In general, execution time for any system to be implemented in a lab workflow should be low enough to not present an additional bottleneck to diagnosis. Therefore, the proposed system was designed to be parallelizable across whole slide images to enhance throughput and meet the efficiency demands of the real-world system. For the reduction to practice, on a single compute node, the median processing time per slide was 2.5 minutes, with overall throughput of 40 whole slide images per hour.

The reduction to practice and the above results demonstrate the ability of a multi-site generalizable pathology deep learning system to accurately classify the majority of specimens in a typical dermatopathology lab workflow. Developing a deep-learning-based classification which translates across image sets from multiple labs is non-trivial. Without compensation for image variations, non-biological differences between data from different labs are more prominent in feature space than biological differences between pathologies. This is demonstrated by image 402 of FIG. 4, in which the image patches cluster according to the lab that prepared and scanned the corresponding slide. When image adaptation is performed prior to computing image features, the images do not appear to strongly cluster by lab (404 of FIG. 4). The reduction to practice further demonstrates that a pathology deep learning system trained on the single Reference Lab can be effectively calibrated to three additional lab sites. Plots 406, 408, 410, and 412 of FIG. 4 show strong class separation between the four classes, and this class separations strengthens with increasing confidence threshold. Intuitively, low-confidence images cluster at the intersection of the four classes. Strong class separation is reflected also in the ROC curves, which show high AUC across classes and labs, as seen in FIG. 2. AUC increases with increased confidence level, demonstrating the utility of confidence score thresholding as a tunable method for excluding poor model predictions. Plots 202, 204, 206, and 208 of FIG. 2 show relatively worse performance in the Squamous and Other classes, which is reflected in FIG. 4 by some overlap between the two classes in feature space; FIG. 3 also shows some confusion between these two classes, but overall, demonstrates accurate classification of the majority of specimens from each class.

The majority of previous deep learning systems in digital pathology have been validated only on a single lab or scanner's images, curated datasets that ignored a portion of lab volume within a specialty, tested on small and unrepresentative datasets, ineffectively balanced datasets, excluded images with artifacts or selectively reverse image "ground truth" retrospectively for misclassifications and train patch-based or segmentation-based models while using traditional computer vision or heuristics to arrive at a whole slide prediction. Such methods do not lend themselves to real-world enabled deep learning that is capable of operating independent to the pathologist and prior to pathologist review. Other models may require some human intervention before they can provide useful information about a slide, and therefore do not enable improvements in lab workflow efficiencies. In contrast, embodiments may be trained on all available slides—images with artifacts, slides without tissue on them, slides with poor staining or tissue preparation, slides exhibiting rare pathology and those with little evidence of pathology.

All of this variability in the data itself implicates that embodiments be capable of determining when it is not possible to make a well-informed prediction. This is accomplished with a confidence score, which can be thresholded to obtain better system performance as shown in FIG. 2 and described in detail below in Section I(C). Note that the correlation between system accuracy and confidence was established a priori using only the Reference Lab validation set (see curve 210 of FIG. 2) to fix the three confidence thresholds. Fixing thresholds a priori establishes that they are generalizable. Campanella, G. et al., *Clinical-grade computational pathology using weakly supervised deep learning on whole slide images*, Nature medicine 1 (2019) attempts to set a classification threshold that yields optimal performance; however, they perform this thresholding using the sigmoid output of a model, on the same test set in which they report it yielding 100% sensitivity; therefore they do not demonstrate the generalizability of this tuned parameter. Secondly, as demonstrated by Gal, Y. & Ghahramani, Z., *Dropout as a Bayesian approximation: Representing model uncertainty in deep learning*, International conference on machine learning, 1050-1059 (2016), a model's predictive probability cannot be interpreted as a measure of confidence.

Note that all performance measures (accuracy, AUC) are reported at the level of a specimen, which may consist of several slides, since diagnosis is not reported at the slide level in dermatopathology. All slide-level decisions are aggregated to the specimen level as described herein; this is particularly useful as not all slides within a specimen will contain pathology, and therefore an incorrect prediction can be made if slide-level-reporting is performed. Most known systems have not attempted to solve the problem of aggregating slide-decisions to the specimen level at which diagnosis is performed.

For an embodiment to operate before pathologist' assessment, the entire pipeline should be able to run in a reasonable time period. The compute time profile shown in FIG. 5 demonstrates that embodiments can classify a whole slide image in under three minutes in the majority of cases, which is on the order of time it takes today's scanners to scan a single slide. There was considerable variation in this number due to a large amount of variability in the size of the tissue to be processed. However, it is important to note that this process can be infinitely parallelized across whole slide images to enhance throughput.

Embodiments have the potential to increase diagnostic efficiency in several situations. For example, embodiments can enable dermatologists and general pathologists to know ahead of time which cases could be potentially challenging, and automatically leave them to a subspecialty expert, avoiding unnecessary delays. Further, it is expected that, as a result of pre-sorting cases with an embodiment, time-to-diagnosis can be shortened. Additionally, pathologists might choose to prioritize certain classes that most often contain the critical cases, cases that need to be reviewed earlier in the day due to requiring more examination or additional tests or stains ordered.

In sum, the deep learning system presented delivers accurate prediction, regardless of scanner type or lab, and requires fewer than 500 slides for calibration to a new site. Some embodiments are capable of assessing which of their decisions are viable based on a computed confidence score, described below in Section I(C) and thereby can filter out decisions that are unlikely to be correct. Furthermore, the classification performed by some embodiments enables development of accessory machine learning models which narrow down a diagnosis within each class. This might enable further prioritization of extreme cases, such as those presenting features of melanoma. The techniques presented herein—for example, deep learning of heterogeneously-composed classes and confidence-based prediction screening—are not limited to application in dermatopathology or even pathology, but broadly demonstrate potentially effective strategies for translational application of deep learning in medical imaging. This confidence based strategy is broadly applicable for achieving the low error rates necessary for practical use of machine learning in challenging and nuanced domains of medical disciplines.

Figure 6:
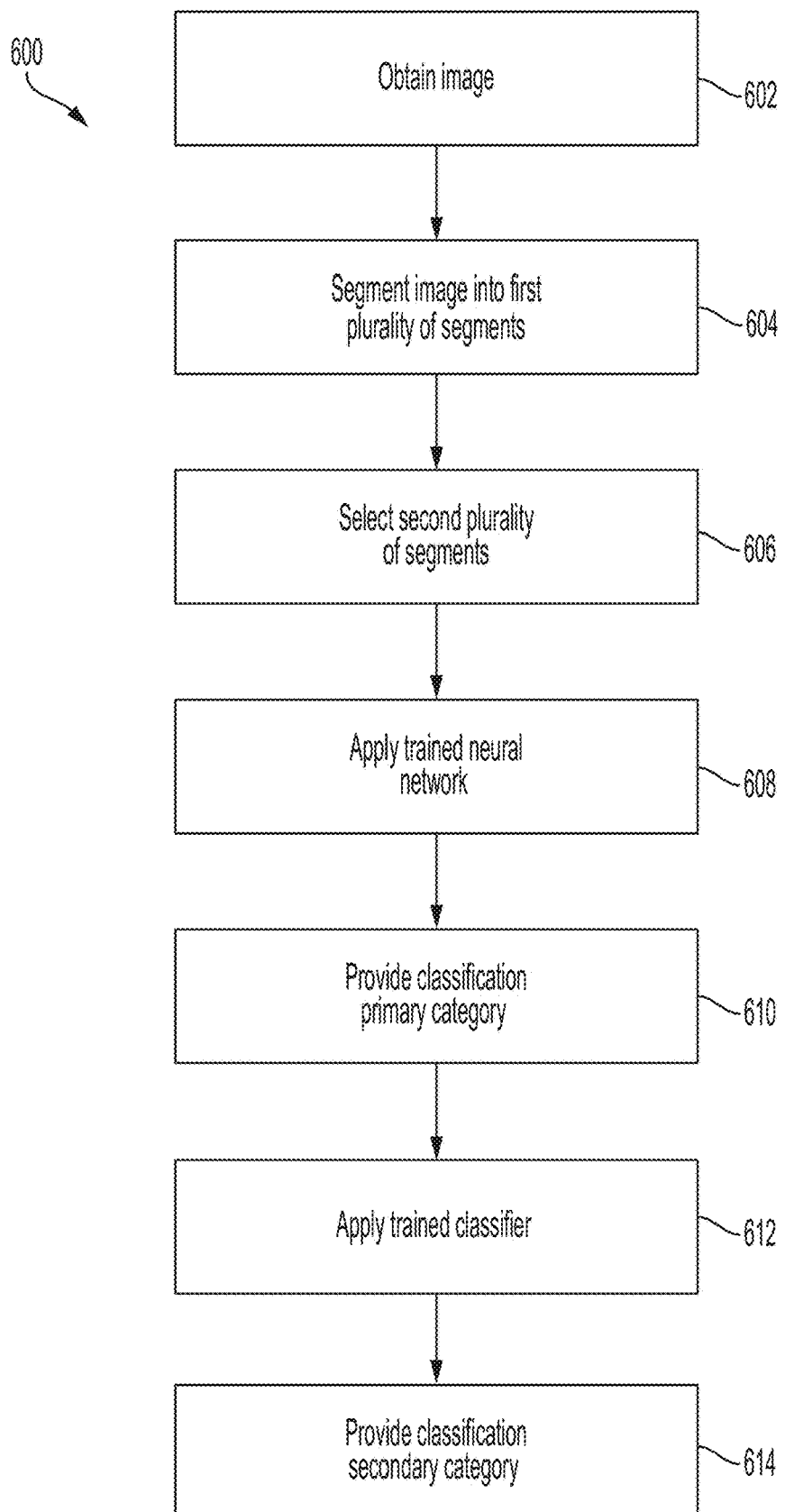
FIG. 6 is a flow chart for a method of automated whole slide image classification using deep learning according to various embodiments.

FIG. 6 is a flow chart for a method 600 of automated whole slide image classification using deep learning according to various embodiments. Method 600 may be performed by a computer system that include at least one electronic processor and electronic persistent memory, coupled to the at least one electronic processor, that includes instructions that configure the at least one electronic processor to perform the actions of method 600. For example, method 600 may be implemented using system 100 of FIG. 1.

Method 600 accepts an image, such as a whole-slide image, and may output one or both of a primary pathology classification and a secondary pathology classification. The primary pathology classification may be one of basaloid patterns class, squamous patterns class, melanocytic patterns class, or other patterns class.

The secondary pathology classification may be a specific diagnosis within a respective primary pathology classification. Thus, for a primary basaloid patterns classification, the secondary classification may be one of: nodular basal cell carcinoma, multicentric basal cell carcinoma, basal cell carcinoma, ulcerative basal cell carcinoma, infiltrative basal cell carcinoma, or remaining basaloids. For a primary melanocytic patterns classification, the secondary classification may be one of: dysplastic nevus, compound nevus, dermal nevus, lentigo, junctional nevus, malignant melanoma, or remaining melanocytic. For a primary squamous patterns classification, the secondary classification may be one of: squamous cell carcinoma, seborrheic keratosis, verruca, actinic keratosis, lichenoid keratosis, or remaining squamous cell carcinomas. For a primary other patterns classification, the secondary classification may be one of: epidermal inclusion cyst, spongiotic dermatitis, scar, fibroepithelial polyp, other dermatitis, or remaining otheres.

At 602, method 600 obtains an image, such as a whole slide image. The whole slide image itself may contain multiple images. The whole slide image may be of a tissue specimen.

At 604, method 600 segments the obtained image into a first plurality of segments, e.g., using computer vision such as Otsu's thresholding or using a convolutional neural network.

Subsequent to 604, method 600 may optionally perform image adaptation, such as stain normalization, as described in detail below in Section II.

At 606, method 600 selects a second plurality of segments from among the first plurality of segments that includes at least one region of interest. A convolutional neural network, such as CNN-1 (108) as shown and described herein in reference to FIG. 1 may be used.

At 608, method 600 applies a trained convolutional neural network to obtain an output primary pathology class, which may be one of the four classes shown and described above in reference to FIGS. 1-4. The neural network may thus be trained by a training corpus comprising a set of pluralities of tissue sample image segments, each of the pluralities of tissue sample image segments comprising image segments from within the same tissue sample image, each of the pluralities of tissue sample image segments labeled according to one of a plurality of primary pathology classes (e.g., basaloid, melanocytic, squamous, or other). The plurality of primary pathology classes may thus consist of a plurality of majority primary pathology classes, where the plurality of primary pathology classes collectively include a majority of pathologies of a particular tissue type according to prevalence. The plurality of primary pathology classes may further include a class for tissue sample image segments not in the plurality of majority primary pathology classes.

At 610, method 600 provides the output primary pathology class (e.g., basaloid pattern, melanocytic pattern, squamous pattern, or other pattern). Method 600 may do so by displaying the primary pathology class on a computer screen, emailing it, delivering it to a computing device, delivering it to a clinical workflow, delivering it to a laboratory information system, or delivering it to a report generation system.

At 612, method 600 applies a trained classifier to at least the second plurality of segments selected at 606 to obtain a secondary pathology class. The trained classifier may be configured to further refine the diagnosis within the primary pathology class. Thus, the system may include a first classifier for further refining a primary basaloid patterns classification into a secondary classification of one of: nodular basal cell carcinoma, multicentric basal cell carcinoma, basal cell carcinoma, ulcerative basal cell carcinoma, infiltrative basal call carcinoma, or remaining basaloids. The system may further include a second classifier for further refining a primary melanocytic patterns classification into a secondary classification of one of: dysplastic nevus, compound nevus, dermal nevus, lentigo, junctional nevus, malignant melanoma, or remaining melanocytic. The system may further include a third classifier for further refining a primary squamous patterns classification into a secondary classification of one of: squamous cell carcinoma, seborrheic keratosis, verruca, actinic keratosis, lichenoid keratosis, or remaining squamous cell carcinomas. The system may further include a fourth classifier for further refining a primary other patterns classification into a secondary classification of one of: epidermal inclusion cyst, spongiotic dermatitis, scar, fibroepithelial polyp, other dermatitis, or remaining others. Known techniques may be used to generate and train these secondary classifiers. Thus, the trained classifier of 612 may be trained by a training corpus that includes a set of secondary pluralities of tissue sample image segments, each set of secondary pluralities comprising image segments from within the same tissue sample image, each set of secondary pluralities labeled according to some pathology subcategory within the classification primary pathology category.

At 614, method 608 provides the secondary pathology class. Method 600 may do so by displaying the primary pathology class on a computer screen, emailing it, delivering it to a computing device, delivering it to a clinical workflow, delivering it to a laboratory information system, or delivering it to a report generation system.

C. Confidence Level Thresholding

The reduction to practice described above was developed entirely using 5,070 whole slide images from a single Reference Lab. Since there is a large amount of variety in both the presentation of skin lesion pathology as well as scanner or preparation-induced abnormalities, the model may assess a confidence for each decision; thereby, likely-misclassified images can be flagged as such. Embodiments may set confidence thresholds a priori based only on performance on the validation set of the Reference Lab (or its analog in new embodiments), which is independent of the data for which the measures of system performance were reported.

In general, Gal, Y. & Ghahramani, Z., Dropout as a Bayesian approximation: Representing model uncertainty in deep learning, International conference on machine learning, 1050-1059 (2016) suggests that the predictive probability obtained from a classifier is a single point estimate, and therefore cannot be reliably interpreted as a measure of prediction confidence. This paper also proposes a method to reliably measure the uncertainty of a decision made by a classifier. Embodiments may adapt this technique to use it for confidence scoring of the decision.

To determine a confidence score for a whole slide image, embodiments may perform a prediction on the same whole slide image repeatedly (e.g., using CNN-3, 111) for several times by omitting a random subset of neurons (e.g., 70%, or more generally any number between 50% and 99%) from the prediction. The subsets may be selected randomly or pseudorandomly. Each repetition results in a prediction made using a different subset of feature representations. The reduction to practice used T=30 repetitions, where each repetition, I, yields a prediction $P_i$, vector of sigmoid values of length equal to the number of classes, however any number of repetitions between 10 and 100 times may be used. Each element of $P_i$ represents the binary probability, $p_{i,c}$ of the corresponding whole slide image belonging to class c. The confidence score s for a given whole slide image may then computed as follows, by way of non-limiting example:

$$s = \max_c \left( \frac{\sum_{i=1}^{T} p_{i,c}}{T} \right)$$

The class associated with the highest confidence s is the predicted class for the whole slide image; finally, the specimen prediction is assigned as the maximum-confidence prediction of its constituent whole slide image predictions. If a specimen's confidence score is below a certain threshold, then the prediction is considered unreliable and the specimen remains unclassified.

Three threshold values for the confidence score were selected for analysis of the reduction to practice as shown and described herein in reference to FIGS. 1-5; these were determined during the development phase, using only the Reference lab's data, because this confidence threshold qualifies as a tunable model parameter. Confidence thresholds were selected such that discarding specimens with sigmoid confidence lower than the threshold yielded a set accuracy in the remaining specimens of the validation set of the Reference Lab. The three target accuracy levels were 90%, 95% and 98% (see FIG. 2); the corresponding sigmoid confidence thresholds of 0.33, 0.76, and 0.99 correspond to confidence Levels 1, 2, and 3 respectively; these confidence thresholds were held fixed, and applied without modification to the test sets from the three test labs.

Embodiments may determine a confidence level for classifications, such as the primary pathology class, as follows. According to various embodiments, during classification, means (or other averages) of sigmoids for each classification over a plurality (e.g., 30, or more generally any number between 10 and 100) reduced-neuron (e.g., 70% of the neurons, or more generally any number between 50% and 99%) iterations may be compared, and a maximum may be selected as indicating the classification, e.g., into a primary classification class. That is, the class corresponding to the maximum averaged sigmoid may be selected as the classification class. Some embodiments may further utilize such sigmoid values for comparisons to threshold values corresponding to confidence levels. If a sigmoid value for a given classification is at least a great as such a threshold, then the classification is accurate with a known level of confidence corresponding to the threshold sigmoid value. This process is shown and described in detail presently in reference to FIG. 7.

Figure 7:
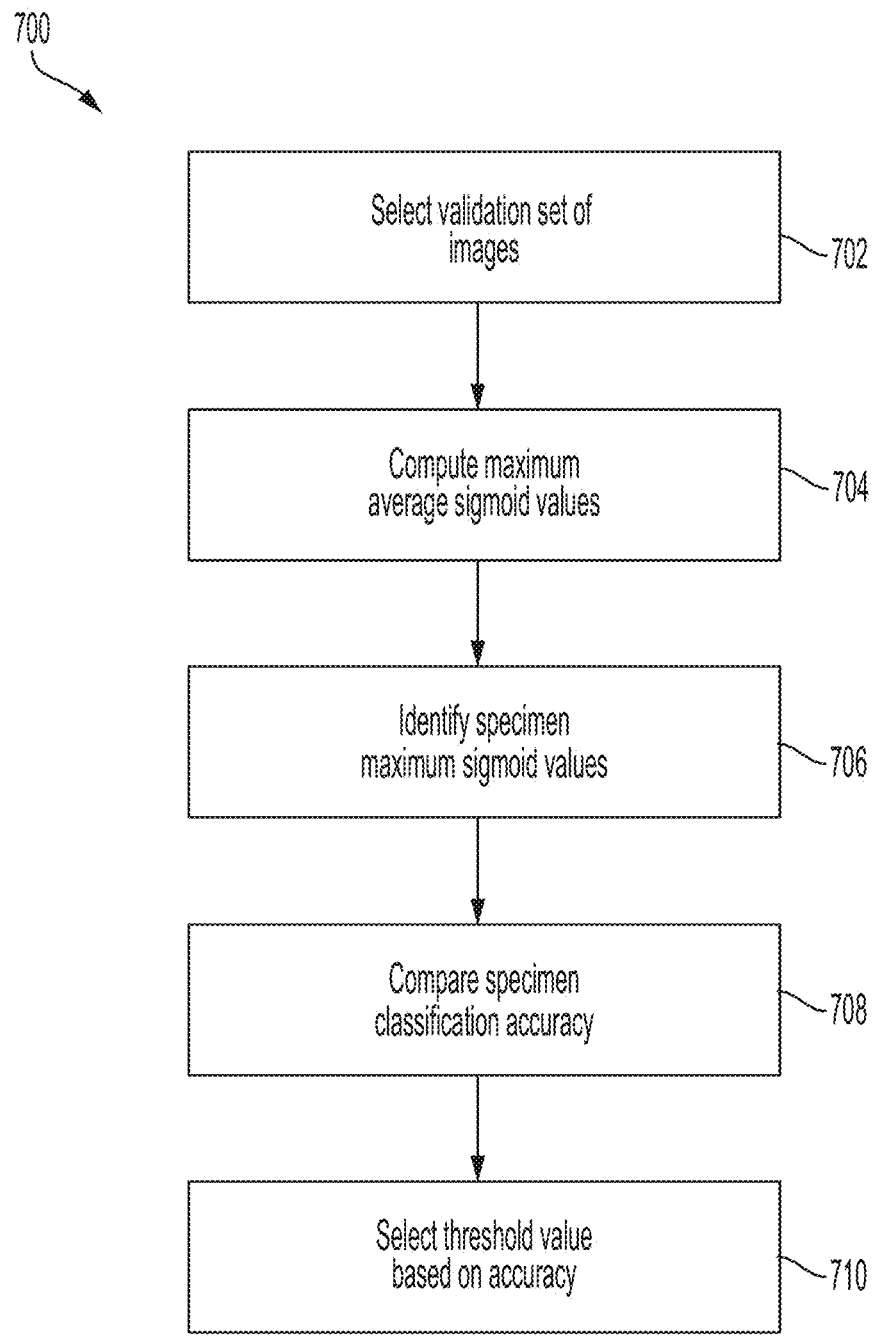
FIG. 7 is a flow diagram for a method of determining a threshold corresponding to a confidence level for classifications according to various embodiments.

FIG. 7 is a flow diagram for a method 700 of determining a threshold corresponding to a confidence level for classifications according to various embodiments. According to various embodiments, selecting a threshold for the maximum averaged sigmoid value that corresponds to a particular confidence for the classification may be performed empirically, as partially illustrated by receiver operating characteristic curve 212 of FIG. 2, above. Such selecting per method 700 may proceed as follows.

At 702, a validation set of classified images for a collection of specimens is selected. Each image in the validation set of images may have an assigned (e.g., human assigned) classification. The validation set may be for a number of specimens, with multiple images (e.g., 1-5) in the validation set for each specimen. For example, the validation set of images may include 700 images of 500 specimens. The validation set may be selected to have been produced by the same lab that generated the training images during the training phase.

At 704, the maximum averaged sigmoid values for each image in the validation set of images is computed. This may be accomplished by applying an embodiment to each image in the validation set of images to a trained neural network as disclosed herein. Such application produces a classification and a corresponding maximum averaged sigmoid value for each image.

At 706, identify the maximum averaged sigmoid value for each specimen depicted in the validation set of images by, for example, selecting the maximum such value over the images (e.g., 1-5 images) in the validation set of images that correspond to a given specimen. At this point, each specimen with images in the validation set of images has an associated maximum averaged sigmoid value and an associated classification accuracy, which may be either "1" to indicate correct classification or "0" to indicate incorrect classification.

At 708, plot (or otherwise compare) the classification accuracy of the specimens represented in the validation set versus a plurality of hypothetical threshold values. That is, for each hypothetical threshold value, plot (or otherwise obtain) a classification accuracy value (e.g., a percentage) for only those specimens having a corresponding maximum averaged sigmoid value that is at least as great as the hypothetical threshold value. (An example curve 210 is provided in FIG. 2.)

At 710, select a threshold value from the hypothetical threshold values that has a corresponding accuracy of specimen classification. For example, as depicted by curve 210 of FIG. 2, for the reduction to practice, a threshold value of about 0.3 corresponds to a 90% accurate classification of the specimens in the validation set.

To use the threshold value, compare a maximum averaged sigmoid value resulting from classifying a novel image to the threshold. If greater, then the image is classified correctly with a confidence level related to the validation set classification accuracy for the selected threshold value. For example, for a hypothetical threshold value of 0.3 corresponding to a 90% accurate classification of the specimens in the validation set, and for a maximum averaged sigmoid value for a novel image of, say, 0.321, the classification value is greater than the threshold value.

In practice, in one dataset, when a classification value exceeds a threshold value corresponding to 90% accurate validation set specimen classification, the accuracy of the novel classification has been determined to be 83%.

II. Stain Normalization

A. Introduction

Because the appearance of a whole slide image varies from lab to lab, scanner to scanner, with the same scanner over time, and even varies based on the brand of stain used, images acquired from different labs or scanners should be adapted before they are interpretable by a model which is trained on the variations of a single lab or image appearance. There are not currently any methods of correcting any of the whole slide image variation factors as described above in the Background section in terms of pre-processing images to be assessed by a deep learning system. Embodiments may be used to solve such problems, as described presently.

B. Stain Normalization and Other Augmentation

Due to the inconsistency of traditional machine-learning-based approaches (the state of the art in stain normalization right now), some embodiments utilize deep learning. There are several existing methods of handling stain variation using deep learning (e.g., StainGANs), but Generative Adversarial Networks (GANs) are notoriously difficult to train.

R. Zhang, P. Isola, and A. A. Efros, "Colorful image colorization," European Conference on Computer Vision, pp. 649-666, Springer, 2016, hereinafter, "Zhang", presents a technique for learning the colors of black-and-white photographs. Zhang trained a model to learn colors from black-and-white photos, using only the lightness channel of a 'Lab' color space image as input. Zhang's deep learning model was adapted and utilized for an entirely different purpose according to various embodiments. In particular, some embodiments utilize such an adapted model in the histopathology domain in order to learn to predict the stain, based only on the lightness channel of the image. In further contrast to Zhang, some embodiments restrict the range of possible colors to the range of those exhibited by the H&E-stains from a single lab. By training a neural network using data from a single lab (input is the lightness channel of the patches from the training site's data, and outputs are quantized 'a' and 'b' channels of the corresponding images which represent color), some embodiments can learn to predict the lab's staining pattern based on the features of the lightness channel. Then, when this model is used for prediction on lab 2, the model takes the lightness channel and predicts a stain for it which is similar to that of lab 1.

In addition to stain, some embodiments address some of the other components of inter-lab image variation with a model setup similar to colorization. To do this, some embodiments utilize augmentation during the training of the model. By adding noise to the input images, jittering hue, saturation, brightness and contrast, and modifying the rotation of the input to the colorization model, such embodiments may account for some of these differences in both tissues themselves as well as scanner properties. These augmentations are not applied to the outputs of the colorization model (channels, 'a' and 'b' which represent color), with the exception of rotation. By learning to predict the original image, which did not receive augmentations, such a model learns to adapt or map an input image to an expected image appearance. Due to this alteration of image properties, this process may be referred to as "adaptation" since it is not a straightforward normalization.

Some embodiments transform images from a new source to have appearance similar to images from the original source, such that a deep learning model has no drop in accuracy when classifying images from the new source.

Some embodiments provide a deep-learning-based method of preprocessing image inputs to a deep learning model by transforming the images themselves into a space that shares the visual characteristics of the original training set. (This is related to domain adaptation, but rather than transforming the diagnosis model to work on a new domain, the model's input itself is transformed into the domain that the model already recognizes).

During training, the input to this model is a set of images which have had their characteristics randomly perturbed, and the output is the original images. During prediction, the input is an image from another lab (unperturbed), and the output predicted is what the image would look like if it were to have come from the original lab with which the model was trained. The effect of this model is to enable accurate prediction with subsequent deep-learning-based classification models which were trained on only a single type of images (in this case, images from a single lab and scanner). A description of this process is shown and described presently in reference to FIG. 8.

Figure 8:
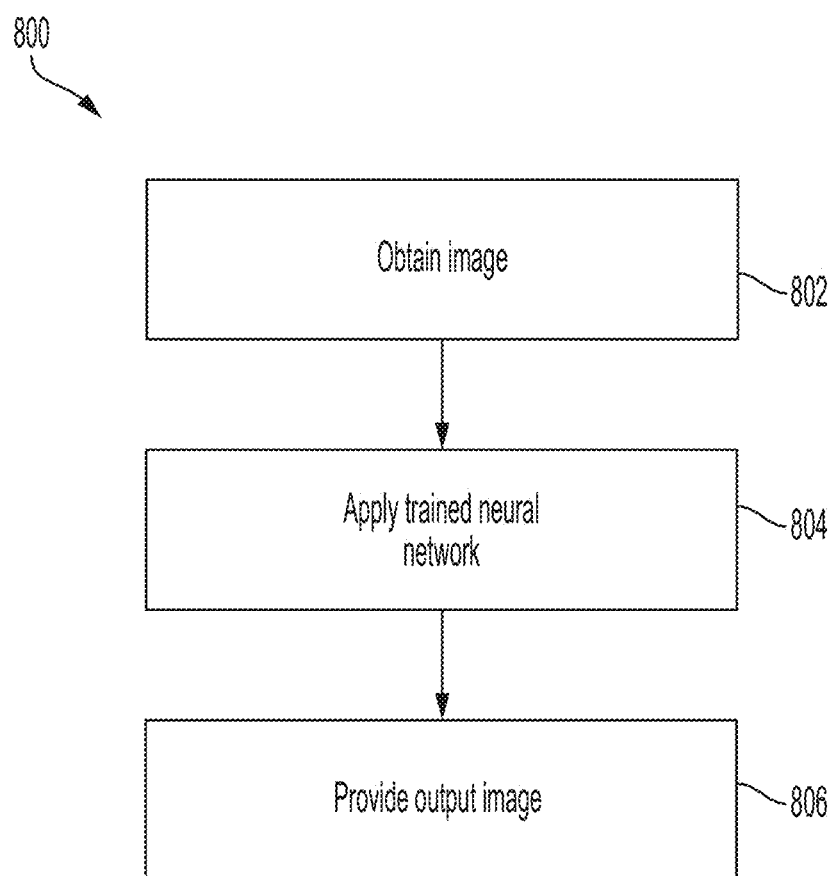
FIG. 8 is a high-level flow diagram of a method for stain normalization using deep learning according to various embodiments.

FIG. 8 is a high-level flow diagram of a method 800 for stain normalization using deep learning according to various embodiments. Method 800 may be performed by a computer system that include at least one electronic processor and electronic persistent memory, coupled to the at least one electronic processor, that includes instructions that configure the at least one electronic processor to perform the actions of method 800. For example, method 800 may be implemented using system 100 of FIG. 1, particularly as CNN-1 (106).

At 802, method 800 obtains a digitized biological tissue image. The image may be a whole slide image. The whole slide image itself may contain multiple images. The shole slide image may be of a tissue specimen.

At 804, method 800 applies, to at least a portion of the digitized biological tissue image, a convolutional neural network trained for stain normalization (and possibly additional image augmentation operations). The convolutional neural network may by trained using a training corpus that includes a plurality of pairs of images, wherein each pair of images of the plurality of pairs of images includes a first image restricted to a lightness axis of a color space and a second image restricted to at least one of: a first color axis of the color space and a second color axis of the color space. Each pair of images may include a first image restricted to a lightness axis of a Lab color space and a second image restricted to an axis 'a' of the Lab color space and to an axis 'b' of the Lab color space. Each second image may be restricted to colors of hematoxylin and eosin. The plurality of pairs of images may include a particular plurality of pairs of images, where each pair of images of the particular plurality of pairs of images comprises a first image that has had noise (e.g., hue noise, saturation noise, brightness noise, contrast noise, or intensity noise) added to it. The plurality of pairs of images may include a rotated plurality of pairs of images, where each pair of images of the rotated plurality of pairs of images includes a first image that has been rotated by an amount, and a second image that has been rotated by the amount. The training corpus may consist of pairs of images derived from images obtained by a single laboratory. The applying causes an output image to be produced, where the output image has been stain normalized and possibly additionally augmented.

At 806, method 800 provides the output image. The image may be provided by displaying it on a computer monitor, sending it in an email, sending it to a computer system, or providing it to a process (e.g., method 600 of FIG. 6) that uses an electronic trained classifier (e.g., CNN-3, 111) that is trained to identify at least one human biological tissue pathology such as a human dermatopathology Thus, some embodiments provide a system for, and a method of, stain normalization image processing for digitized biological tissue images. Such embodiments may obtain a digitized biological tissue image. Such embodiments may apply to at least a portion of the digitized biological tissue image an at least partially computer implemented convolutional neural network trained using a training corpus comprising a plurality of pairs of images, where each pair of images of the plurality of pairs of images comprises a first image restricted to a lightness axis of a color space and a second image restricted to at least one of: a first color axis of the color space and a second color axis of the color space, such that the applying causes an output image to be produced. Such embodiment may provide the output image, e.g., to a system or method of automated whole-slide image classification using deep learning such as disclosed in Section I, or by displaying on a computer monitor. More particularly, an embodiment may be used as CNN1 (106) of FIG. 1.

Certain embodiments can be performed using a computer program or set of programs. The computer programs can exist in a variety of forms both active and inactive. For example, the computer programs can exist as software program(s) comprised of program instructions in source code, object code, executable code or other formats; firmware program(s), or hardware description language (HDL) files. Any of the above can be embodied on a transitory or non-transitory computer readable medium, which include storage devices and signals, in compressed or uncompressed form. Exemplary computer readable storage devices include conventional computer system RAM (random access memory), ROM (read-only memory), EPROM (erasable, programmable ROM), EEPROM (electrically erasable, programmable ROM), and magnetic or optical disks or tapes.

While the invention has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method can be performed in a different order than illustrated or simultaneously. Those skilled in the art will recognize that these and other variations are possible within the spirit and scope as defined in the following claims and their equivalents.

What is claimed is:

1. A computer-implemented method of classifying a tissue specimen, the method comprising:
   obtaining a computer readable image of the tissue specimen;
   segmenting the image into a first plurality of segments;
   selecting, from among the first plurality of segments, a second plurality of segments that include at least one region of interest;
   applying, to the second plurality of segments, an electronic convolutional neural network trained by a training corpus comprising a set of pluralities of tissue sample image segments, each of the pluralities of tissue sample image segments comprising image segments from within a same tissue sample image, each of the pluralities of tissue sample image segments labeled according to one of a plurality of primary pathology classes, wherein the plurality of primary pathology classes consist of a plurality of majority primary pathology classes, wherein the plurality of majority primary pathology classes collectively comprise a majority of pathologies of a particular tissue type according to prevalence, and a class for tissue sample image segments not in the plurality of majority primary pathology classes, whereby a primary pathology classification is output; and
   providing the primary pathology classification.

2. The method of claim 1, further comprising:
   applying, to at least a portion of the second plurality of segments, a trained classifier trained by a training corpus comprising a set of secondary pluralities of tissue sample image segments, each set of secondary pluralities comprising image segments from within a same tissue sample image, each set of secondary pluralities labeled according to some pathology subclass within the primary pathology classification, whereby a secondary pathology classification is output; and
   providing the secondary pathology classification.

3. The method of claim 1, wherein the primary pathology classification is provided to at least one of: a clinical workflow, a laboratory information system, or a report generation system.

4. The method of claim 1, wherein the plurality of majority primary pathology classes comprise at least one of: basaloid patterns class, squamous patterns class, or melanocytic patterns class.

5. The method of claim 1, wherein the class for tissue sample image segments not in the plurality of majority primary pathology classes comprises tissue sample image segments for at least one of: ulcerations, epidermal inclusion cysts, or scars.

6. The method of claim 1, wherein the applying, to the second plurality of segments, the electronic convolutional neural network comprises:
applying, to the second plurality of segments, the electronic convolutional neural network a plurality of times, each time using a different proper subset of neurons in the electronic convolutional neural network, whereby a plurality of predictions within each of the primary pathology classes are produced;
combining, within each of the primary pathology classes, a respective plurality of predictions, whereby a combined prediction for each of the primary pathology classes is produced; and
selecting a main combined prediction as the primary pathology classification.

7. The method of claim 6, wherein each different proper subset of neurons in the electronic convolutional neural network consists of less than or equal to a selected value of between 50% and 99% of neurons in the electronic convolutional neural network.

8. The method of claim 6, wherein the plurality of times comprises a number of times selected from the range from 10 times to 100 times.

9. The method of claim 6:
wherein the combining, within each of the primary pathology classes, the respective plurality of predictions, comprises determining a mean of sigmoid function outputs for respective pluralities of predictions within each of the primary pathology classes; and
wherein the selecting the main combined prediction comprises selecting a maximum mean.

10. The method of claim 9, further comprising determining that the maximum mean exceeds a threshold value, wherein the threshold value represents a mean of sigmoid function outputs, for a plurality of validation images of tissue specimens with known diagnoses according to the plurality of primary pathology classes, corresponding to a selected confidence level.

11. A system for classifying a tissue specimen, the system comprising at least one electronic processor and at least one persistent electronic memory communicatively coupled to the at least one electronic processor, the at least one persistent memory comprising computer readable instructions that, when executed by the at least one electronic processor, configure the at least one electronic processor to perform operations comprising:
obtaining a computer readable image of the tissue specimen;
segmenting the image into a first plurality of segments;
selecting, from among the first plurality of segments, a second plurality of segments that include at least one region of interest;
applying, to the second plurality of segments, an electronic convolutional neural network trained by a training corpus comprising a set of pluralities of tissue sample image segments, each of the pluralities of tissue sample image segments comprising image segments from within a same tissue sample image, each of the pluralities of tissue sample image segments labeled according to one of a plurality of primary pathology classes, wherein the plurality of primary pathology classes consist of a plurality of majority primary pathology classes, wherein the plurality of majority primary pathology classes collectively comprise a majority of pathologies of a particular tissue type according to prevalence, and a class for tissue sample image segments not in the plurality of majority primary pathology classes, whereby a primary pathology classification is output; and
providing the primary pathology classification.

12. The system of claim 11, wherein the operations further comprise:
applying, to at least a portion of the second plurality of segments, a trained classifier trained by a training corpus comprising a set of secondary pluralities of tissue sample image segments, each set of secondary pluralities comprising image segments from within a same tissue sample image, each set of secondary pluralities labeled according to some pathology subclass within the primary pathology classification, whereby a secondary pathology classification is output; and
providing the secondary pathology classification.

13. The system of claim 11, wherein the primary pathology classification is provided to at least one of: a clinical workflow, a laboratory information system, or a report generation system.

14. The system of claim 11, wherein the plurality of majority primary pathology classes comprise at least one of: basaloid patterns class, squamous patterns class, or melanocytic patterns class.

15. The system of claim 11, wherein the class for tissue sample image segments not in the plurality of majority primary pathology classes comprises tissue sample image segments for at least one of: ulcerations, epidermal inclusion cysts, or scars.

16. The system of claim 11, wherein the applying, to the second plurality of segments, the electronic convolutional neural network comprises:
applying, to the second plurality of segments, the electronic convolutional neural network a plurality of times, each time using a different proper subset of neurons in the electronic convolutional neural network, whereby a plurality of predictions within each of the primary pathology classes are produced;
combining, within each of the primary pathology classes, a respective plurality of predictions, whereby a combined prediction for each of the primary pathology classes is produced; and
selecting a main combined prediction as the primary pathology classification.

17. The system of claim 16, wherein each different proper subset of neurons in the electronic convolutional neural network consists of less than or equal to a selected value of between 50% and 99% of neurons in the electronic convolutional neural network.

18. The system of claim 16, wherein the plurality of times comprises a number of times selected from the range from 10 times to 100 times.

19. The system of claim 16:
wherein the combining, within each of the primary pathology classes, the respective plurality of predictions, comprises determining a mean of sigmoid function outputs for respective pluralities of predictions within each of the primary pathology classes; and
wherein the selecting the main combined prediction comprises selecting a maximum mean.

20. The system of claim 19, wherein the operations further comprise determining that the maximum mean exceeds a threshold value, wherein the threshold value represents a mean of sigmoid function outputs, for a plurality of validation images of tissue specimens with known diagnoses according to the plurality of primary pathology classes, corresponding to a selected confidence level.

* * * * *